United States Patent [19]

Murao et al.

[11] Patent Number: 4,837,337

[45] Date of Patent: Jun. 6, 1989

[54] PROCESS FOR PRODUCING PYRROLIDONE DERIVATIVE

[75] Inventors: Yoshikazu Murao, Machida; Masao Miyake, Yokohama, both of Japan

[73] Assignee: Mitsubishi Chemical Industries Limited, Tokyo, Japan

[21] Appl. No.: 151,589

[22] Filed: Feb. 3, 1988

Related U.S. Application Data

[63] Continuation-in-part of Ser. No. 804,757, Dec. 5, 1985, abandoned.

[30] Foreign Application Priority Data

Dec. 15, 1984 [JP] Japan ................................. 59-264845
Jan. 23, 1985 [JP] Japan ................................. 60-10374
Jun. 17, 1985 [JP] Japan ................................. 60-131505
Jun. 17, 1985 [JP] Japan ................................. 60-131506

[51] Int. Cl.$^4$ .......................................... C07D 207/27
[52] U.S. Cl. ................................................. 548/551
[58] Field of Search ........................................ 548/551

[56] References Cited

U.S. PATENT DOCUMENTS 2,924,606  2/1960  Schroeder et al. .............. 260/326.5
3,853,910 12/1974  Freyermuth et al. ................ 548/551
3,956,313  5/1976  Freyermuth et al. ................ 548/551

FOREIGN PATENT DOCUMENTS 1078576  3/1960  Fed. Rep. of Germany .
3544134  6/1986  Fed. Rep. of Germany .

OTHER PUBLICATIONS

Organic Reactions, vol. 14, pp. 92–103, "α-Amidoalkylations at Carbon"(1965).
Bohme und Berg; "Zur Kenntnis de N-[αAlkoxy-alkyl]-carbonsaureamide . . . ", pp. 2127–2135 (1966).

*Primary Examiner*—David B. Springer
*Attorney, Agent, or Firm*—Oblon, Spivak, McClelland, Maier & Neustadt

[57] ABSTRACT

Disclosed herein is a process for producing a pyrrolidone derivative represent by the general formula (I):

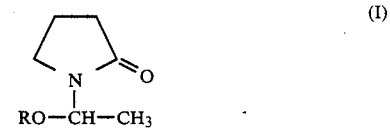

wherein R is an organic residue obtained by removing hydroxy radical from a $C_{1-10}$ primary alcohol, $C_{1-10}$ secondary alcohol or derivative thereof, comprising (1) reacting 2-pyrrolidone with acetaldehyde in the presence of a catalyst, thereby obtaining N-(α-hydroxyethyl)pyrrolidone, and (2) reacting the thus obtained N-(α-hydroxyethyl)pyrrolidone with a primary alcohol, a secondary alcohol or a derivative thereof in the presence of an acidic catalyst to obtain the pyrrolidone derivative.

15 Claims, No Drawings

PROCESS FOR PRODUCING PYRROLIDONE DERIVATIVE

CROSS REFERENCE TO RELATED APPLICATION

The present invention is a continuation-in-part to U.S. patent application Ser. No. 804,757 filed on Dec. 5, 1985, abandoned.

BACKGROUND OF THE INVENTION

The present invention relates to a process for producing a pyrrolidone derivative represent by the general formula (I):

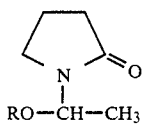

wherein R is an organic residue obtained by removing hydroxy radical from a $C_{1-10}$ primary alcohol, $C_{1-10}$ secondary alcohol or derivative thereof, by reacting acetaldehyde with 2-pyrrolidone, thereby containing N-(α-hydroxyethyl)pyrrolidone and reacting with a primary alcohol, a secondary alcohol or a derivative thereof with the thus obtained N-(α-hydroxyethyl)pyrrolidone to obtain the object product, the pyrrolidone derivative represented by the formula (I).

N-(α-hydroxyethyl)pyrrolidone and N-(α-alkoxyethyl)pyrrolidone are the useful starting materials for the synthesis of N-vinylpyrrolidone along the following reaction formula.

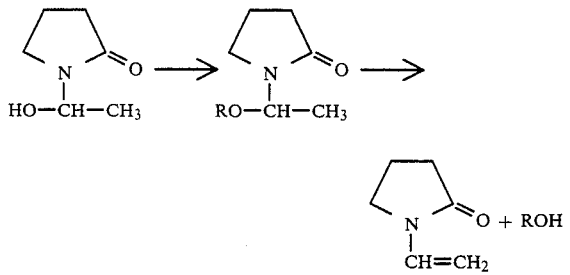

As a process for producing N-(α-alkoxyethyl)pyrrolidone, (1) a process for producing N-(α-ethoxyethyl)pyrrolidone by reacting diethylacetal with 2-pyrrolidone (yield: 34%) (refer to Ber. Vol. 99,2128,1965), and (2) a process for producing N-(α-methoxyethyl)pyrrolidone by reacting α-chloroethyl methyl ether with 2-pyrrolidone (yield: 78%) (refer to Japanese Patent Application Laid-Open No. 56-75464 (1971)) have been hitherto known.

However, these processes are not industrially satisfactory, because the yield of the process (1) is low and the industrial utilization of the starting material of the process (2) is difficult.

On the other hand, a process for producing N-(α-hydroxyethyl)cyclic amide has been known. For instance, in Japanese Patent Publication No. 45-14283(1970), a process wherein acetaldehyde is reacted with a secondary cyclic amide by liquid-liquid contact in the presence of an acidic catalyst or basic catalyst, thereby containing N-(α-hydroxyethyl)cyclic amide and the thus obtained N-(α-hydroxyethyl)cyclic amide is subjected to thermal decomposition to obtain N-vinylamide, has been disclosed.

However, there is a problem in the process that the yield of the thus produced N-(α-hydroxyethyl)pyrrolidone is low. For instance, Example 3 of the Japanese Patent Publication only discloses the yield of the final product, N-vinylpyrrolidone, however, even in the case where the rate of conversion of N-(α-hydroxyethyl)pyrrolidone to N-vinylpyrrolidone by thermal decomposition is assumed to be 100%, there is a problem that the yield of N-(α-hydroxyethyl)pyrrolidone is only about 50%.

As a result of the present inventors' studies concerning a process for producing a pyrrolidone derivative useful for the synthesis of N-vinylpyrrolidone in a higher yield than that of the hitherto-known methods, the present inventors have found that an object of the present invention is easily achieved by (1) reacting acetaldehyde with 2-pyrrolidone in the presence of a catalyst (hereinafter referred to as "the first step"), thereby obtaining N-(α-hydroxyethyl)pyrrolidone and (2) reacting the thus obtained N-(α-hydroxyethyl)pyrrolidone with a primary alcohol, a secondary alcohol or a derivative thereof in the presence of a acidic catalyst (hereinafter referred to as "the second step"), and the present invention has been attained based on the above-mentioned finding.

SUMMARY OF THE INVENTION

In an aspect of the present invention, there is provided a process for producing a pyrrolidone derivative represented by the general formula (I):

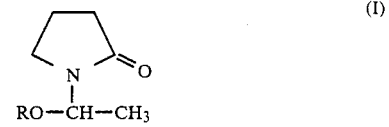

wherein R is an organic residue obtained by removing hydroxy radical from a $C_{1-10}$ primary alcohol, $C_{1-10}$ secondary alcohol or derivative thereof, comprising:

(1) reacting 2-pyrrolidone with acetaldehyde in the presence of a catalyst which is at least one member selected from the group consisting of potassium carbonate, sodium carbonate, potassium phosphate, sodium phosphate, potassium pyrophosphate, sodium pyrophosphate, potassium silicate and sodium silicate in an amount of 0.0001 to 10 mol % of the catalyst per mole of 2-pyrrolidone, thereby obtaining N-(α-hydroxyethyl)pyrrolidone at a temperature in the range of −10° to 60° C.; and (2) reacting the thus obtained N-(α-hydroxyethyl)pyrrolidone with a $C_{1-10}$ primary alcohol, a $C_{1-10}$ secondary alcohol or a derivative thereof in the presence of an acidic catalyst selected from the group consisting of an inorganic acid, sulfamic acid, methanesulfonic acid, ethanesulfonic acid, p-toluenesulfonic acid and an acidic ion-exchange resin used in an amount of 0.001 to 10 mol % of the acidic catalyst per mole of N-(α-hydroxyethyl)pyrrolidone at a temperature in the range of −10° to 100° C.

DETAILED DESCRIPTION OF THE INVENTION

According to the process of the present invention (hereinafter referred to as "the present process"), 2-pyrrolidone is reacted with acetaldehyde in the presence of a catalyst to obtain N-(α-hydroxyethyl)pyrrolidone. The reaction may be carried out in any conventional reaction vessel equipped with a stirrer by introducing 2-pyrrolidone into the reaction vessel, and then supplying acetaldehyde which is in the gaseous state or liquid state, preferably the gaseous state, into the vessel continuously. Although the reaction is ordinarily carried out batchwise, it is possible to carry out the reaction continuously.

The catalyst used in the first step of the present process is a weakly basic salt comprising a strong base and a weak acid showing a pKa of 4 to 15. The pKa is a value of an aqueous solution of the acid of a concentration of 0.01 mol/liter at 25° C. As such a weakly basic salt, for instance, a salt of a strong base such as hydroxides of lithium, sodium and potassium with a weak acid such as organic acids, phenols, sulfurous acid, phosphorous acid, phosphinic acid, pyrophospohoric acid, phosphoric acid, carbonic acid, boric acid, orthosilicic acid, metasilicic acid, etc. may be used. Of the salts, the particularly preferable salts are potassium carbonate, sodium carbonate, potassium phosphate, sodium phosphate, potassium pyrophosphate, sodium pyrophosphate, potassium orthosilicate and sodium orthosilicate.

The ratio of the amount of the catalyst used in the first step of the present process based on the amount of 2-pyrrolidone is generally selected from the range of 0.0001 to 10 mol %, and the preferable range depends on the state of supplying acetaldehyde as a starting material to the reaction system. Namely, in the case of supplying acetaldehyde in a gaseous state (in the manner of supplying acetaldehyde in the gaseous state, acetaldehyde is used after removing acetic acid present in acetaldehyde, as a decomposition material), the ratio thereof is preferably selected from the range of 0.001 to 1 mol %, more preferably from 0.01 to 0.5 mol %.

On the other hand, in the case of supplying acetaldehyde containing acetic acid in the liquid state, it is preferable to carry out the introduction of acetaldehyde in consideration of the coexistence of acetic acid as follows.

Namely, while assuming the amount of acetic acid in acetaldehyde to the amount of 2-pyrrolidone to be X mol %, the amount of the catalyst to the amount of 2-poyrrolidone is selected from the range of (X+0.001) to (X+2) mol %, preferably (X+0.01) to (X+2) mol %. In the case where the amount of the catalyst to the amount of 2-pyrrolidone is below (X+0.001) mol %, the reaction rate is extremely low, and on the other hand, in the case where the amount is over (X+2) mol %, the conversion ratio of 2-pyrrolidone is low.

The reaction is carried out at a temperature selected from the range of −10° to 60° C., preferably 0° to 50° C. In the case where the reaction is carried out at a temperature of over 60° C., both the decomposition of the thus produced N-(α-hydroxyethyl)pyrrolidone and the condensation of acetaldehyde are caused, and on the other hand, in the case of carrying out the reaction at a temperature of below −10° C., the reaction rate is extremely slow.

Although the reaction between 2-pyrrolidone and acetaldehyde can be carried out in the presence or absence of a solvent, it is preferable to carry out the reaction in the presence of a solvent dissolving 2-pyrrolidone in the case where the reaction is carried out at a temperature of below the melting point of 2-pyrrolidone(25° C.). As the solvent, water, alcohols such as methanol, ethanol, etc., aromatic hydrocarbons such as benzene, toluene, xylene, etc., aliphatic hydrocarbons such as n-hexane, etc., alicyclic hydrocarbons such as cyclohexane, etc., ethers such as diethyl ether, tetrahydrofuran, etc. and esters such as ethyl acetate, etc. may be exemplified. The amount of the solvent used in the first step of the present process is suitably selected from the range of 0.01 to 5 times by weight of the amount of 2-pyrrolidone.

The molar ratio of acetaldehyde to 2-pyrrolidone is ordinarily in the range of 0.7 to 2.0, preferably 0.9 to 1.6. In the case where the molar ratio is below 0.7, although the each selectivity of N-(α-hydroxyethyl)pyrrolidone based on 2-pyrrolidone and an acetaldehyde are high, the conversion ratio of 2-pyrrolidone is low. On the other hand, in the case where the molar ratio is over 2.0, although the conversion ratio of 2-pyrrolidone is high, the selectivity of N-(α-hydroxyethyl)pyrrolidone based on acetaldehyde is low.

In addition, the yield in the present process can be raised by precipitating N-(α-hydroxyethyl)pyrrolidone which has been formed during the reaction and thereafter continuing the reaction. The precipitation of N-(α-hydroxyethyl)pyrrolidone is ordinarily carried out in the same reaction vessel in which the reaction between 2-pyrrolidone and acetaldehyde has been carried out, however, the precipitation may be carried out in a different reaction vessel. In the case of carrying out the operation in the same reaction vessel, (i) the reaction system is cooled to a temperature of −20° to 25° C., preferably 0° to 10° C. when the conversion ratio of 2-pyrrolidone becomes 50 to 97 mol %, preferably 60 to 97 mol % and more preferably 70 to 97 mol %, (ii) a small amount of N-(α-hydroxyethyl)pyrrolidone, as the crystal nucleus, is added to the reaction system or (iii) the cooling and the addition are carried out simultaneously in combination, thereby precipitating the crystals of N-(α-hydroxyethyl)pyrrolidone.

Namely, in the case where the conversion ratio of 2-pyrrolidone is below 60 mol %, it is difficult to precipitate the crystals, and on the other hand, in the case where the conversion ratio of over 97 mol %, although the precipitation of the crystals is easily effected, it is not profitable because it is necessary to use a large excess of acetaldehyde for raising the conversion ratio of 2-pyrrolidone over 97 mol %.

In the case of conducting the precipitation of N-(α-hydroxyethyl)pyrrolidone in a reaction vessel different from the original reaction vessel, a small excess amount of acetaldehyde to 2-pyrrolidone is added, and the reaction mixture is transferred to the reaction vessel wherein the precipitation of N-(α-hydroxyethyl)pyrrolidone is effected, when the conversion ratio of 2-pyrrolidone becomes 50 to 90 mol %, preferably 60 to 90 mol %. Or else, after adding acetaldehyde in an amount less than equimolar to 2-pyrrolidone to the reaction mixture, the reaction mixture is transferred to the reaction vessel wherein the precipitation of N-(α-hydroxyethyl)pyrrolidone is effected, and after further adding acetaldehyde in an amount so that the total amount of the thus added acetaldehyde is a little excess to 2-pyrrolidone, N-(α-hydroxyethyl)pyrrolidone is precipitated.

In addition, in the case of precipitating the crystals of N-(α-hydroxyethyl)pyrrolidone, it is preferable to use a dispersing medium which does not dissolve the crystals of N-(α-hydroxyethyl)pyrrolidone but disperse thereof in the system. Such a dispersing medium may be coexistent with the reactants at the starting time of the reaction, or may be added just before the precipitation of the crystals. However, in the case of carrying out the reaction at a temperature of lower than 25° C. and precipitating the crystals, it is preferable to make a dispersing medium which dissolves 2-pyrrolidone and disperses the crystals of N-(α-hydroxyethyl)pyrrolidone without dissolving thereof, coexistent with the reactants at the starting time of the reaction. As the dispersing medium, aliphatic hydrocarbons such as cyclohexane, hexane, heptane, etc. which hardly dissolve both 2-pyrrolidone and N-(α-hydroxyethyl)pyrrolidone, and aromatic hydrocarbons such as benzene, toluene, xylene, etc. which dissolves 2-pyrrolidone but hardly dissolves N-(α-hydroxyethyl)pyrrolidone, ethers such as diethyl ether, tetrahydrofuran, etc. and esters such as ethyl acetate, etc. may be exemplified.

The amount of the dispersing medium for use in the first step of the present process is suitably selected from the range of 0.2 to 3 times by weight of the amount of 2-pyrrolidone.

Alternatively, the yield of N-(α-hydroxyethyl)pyrrolidone can be raised by further supplying acetaldehyde into the reaction mixture instead of cooling and adding the crystal nuclei to the reaction system.

According to the present invention, the thus obtained N-(α-hydroxyethyl)pyrrolidone is reacted with a primary alcohol, a secondary alcohol or a derivative thereof in the presence of an acidic catalyst in the second step of the present process.

In the present application, the derivative of alcohol includes alkylene glycol and ether thereof, polyalkylene glycol and ether thereof, and glycerol.

As the alcohol or the derivative thereof used according to the present invention, although a suitable member may be optionally selected from primary alcohols, a derivative thereof, secondary alcohols and a derivative thereof, $C_{1-10}$ primary alcohol, a derivative thereof, $C_{1-10}$ secondary alcohol and a derivative thereof is preferable, and $C_{1-10}$ aliphatic alcohol is more preferable from the viewpoints of the reactivity of the alcohol or the derivative thereof and the solubility of N-(α-hydroxyethyl)pyrrolidone to the alcohol and the derivative thereof. Although polyvalent alcohol is not preferable, because it gives more than two kinds of reaction products, it does not hinder producing N-vinylpyrrolidone by cleaving the alkoxy group. As the example of preferable primary alcohols, methanol, ethanol, n-propanol, n-butanol, n-pentanol, n-hexanol, n-heptanol, n-octanol, and benzyl alcohol, as the example of secondary alcohols, isopropyl alcohol, isobutanol, and as a derivative of alcohols, 2-methoxyethanol, 2-ethoxyethanol, 2-propoxyethanol, 2-butoxyethanol, diethylene glycol monomethyl ether, ethylene glycol, propylene glycol, 1,4-butanediol, diethylene glycol and glycerol may be exemplified.

The amount of the alcohol or the derivative thereof to N-(α-hydroxyethyl)pyrrolidone may be optionally decided, however, because of the thermal instability of N-(α-hydroxyethyl)pyrrolidone and of the difficulty in recovering N-(α-hydroxyethyl)pyrrolidone after finishing the reaction, it is preferable to use the alcohol or the derivative thereof in an equimolar or larger amount, namely ordinarily 1.0 to 30 times by mol of the amount of N-(α-hydroxyethyl)pyrrolidone. Since N-(α-hydroxyethyl)pyrrolidone is a crystalline compound, it is preferable to use the alcohol or the derivative thereof as a solvent, and in such a case, the amount of the used alcohol or derivative thereof is preferably 2 to 30 times by mol of the amount of N-(α-hydroxyethyl)pyrrolidone.

In order to limit the amount of the alcohol or the derivative thereof used in the reaction as small as possible, a solvent which is inert in the reaction may be suitably used. Even in the case where a part of N-(α-hydroxyethyl)pyrrolidone presents as crystals in the reaction system, it is liquefied after reaction with the alcohol or the derivative thereof and accordingly, the inert solvent used herein may be the substance dissolving N-(α-hydroxyethyl)pyrrolidone or the substance used only for dispersing N-(α-hydroxyethyl)pyrrolidone in the reaction system. In the case of using such a solvent, the amount of the used alcohol or derivative thereof is preferably one to six times by mol of the amount of N-(α-hydroxyethyl)pyrrolidone.

As the catalyst used in the reaction between N-(α-hydroxyethyl)pyrrolidone and the alcohol or the derivative thereof, any one of the ordinary acidic catalysts may be used in general, and for instance, inorganic acids, organic acids, weakly acidic- or strongly acidic ion-exchanging resins, solid acids, etc. may be exemplified, and strongly acidic substances such as sulfuric acid, hydrochloric acid, nitric acid, hydrobromic acid, sulfamic acid, methanesulfonic acid, ethanesulfonic acid, p-toluenesulfonic acid, cross-linked polystyrenesulfonic acid, etc. are preferable. The acidic catalyst is used in an amount of 0.001 to 10 mol % to the amount of N-(α-hydroxyethyl)pyrrolidone ordinarily, and preferably 0.005 to 8 mol %, and more preferably 0.1 to 5 mol %.

In the case where the amount of the catalyst is below 0.001 mol %, the reaction rate is extremely slow, and on the other hand, in the case of over 10 mol %, the yield of the product is low due to the occurrence of side reactions.

In addition, in the case of using a heterogeneous catalyst such as ionexchanging resin, the reaction may be carried out by passing the mixture of the reactants through a column in which the catalyst has been filled.

Although the temperature of reaction between N-(α-hydroxyethyl)pyrrolidone and the alcohol or the derivative thereof may be selected from the range of −10° to 100° C., it is preferable to carry out the reaction at a temperature in the range of from 0° to 80° C. The reaction rate is extremely slow at the temperature of below −10° C., and on the other hand, decomposition of N-(α-hydroxyethyl)pyrrolidone occurs at a temperature of over 100° C., thereby reducing the yield of the pyrrolidone derivative of the formula (I).

In the case where the reaction is carried out in line with the process according to the present invention, it is easy to obtain the pyrrolidone derivative of the formula (I) in a yield of 90 to 98%, and it is more preferable to carry out the reaction while removing water formed in the reaction between N-(α-hydroxyethyl)pyrrolidone and the alcohol on the derivative thereof out of the reaction system, because the yield of the objective product is further improved.

Although the removal of water can be effected ordinarily at an optional temperature in the range of −10° to 80° C., it is preferably carried out at a temperature in the range of 10° to 50° C. The removal of water may be carried out by using any method of the known methods, however, it is preferably carried out by adding a dehydrating agent or by distilling water off from the reaction system. Although an optional dehydrating agent may be ordinarily used, a dehydrating agent of from neutral to acidic nature or preferably a dehydrating agent of from neutral to weakly acidic nature is used. As an example of the preferable dehydrating agent, molecular sieves, calcium chloride, sodium sulfate, magnesium sulfate and calcium sulfate may be exemplified.

The dehydrating agent may be coexistent with the reactants at the starting time of the reaction, and it may be added during the reaction.

Water may be distilled off under an ordinary pressure or a reduced pressure, however, it is preferred to distill water off under a reduced pressure. In the case of carrying out the distillation of water under an ordinary pressure, the reaction temperature frequently elevates over 80° C. even by the use of an azeotropic solvent which boils with water and accordingly it is necessary to carefully carry out distillation of water under ordinary pressure.

In the case where the alcohol or the derivative thereof which is reacted with N-($\alpha$-hydroxyethyl)pyrrolidone is azeotropic with water, water is brought into azeotropic distillation with the alcohol or the derivative thereof, and after separating the alcohol or the derivative thereof from water, the thus separated alcohol or the derivative thereof is added to the reaction mixture or the same amount of new alcohol or derivative thereof as the amount of the respective alcohol or derivative thereof distilled off from the reaction system by azeotropic distillation is added to the reaction mixture. The removal of water by distillation can be also carried out in the presence of a solvent.

As the solvent, a solvent which is distilled azeotropically with water and is easily separated from water is preferably used, and for example, hexane, cyclohexane, heptane and the like may be exemplified.

The amount of the solvent used in the removal of water is selected from the range of 0.01 to 5 times by weight of the amount of N-($\alpha$-hydroxyethyl)pyrrolidone used in the reaction.

Such a solvent may be added preliminarily at the starting time of the reaction of N-($\alpha$-hydroxyethyl)pyrrolidone with the alcohol or the derivative thereof, and may be added just before the distillation of water.

According to the present invention, it is possible to produce the pyrrolidone derivative of the formula (I) in a far higher yield of 90 to 98% than that in the conventional process and with an industrial profitability.

The present invention will be explained more in detail while referring to the following non-limitative examples.

EXAMPLE 1

Synthesis of N-($\alpha$-n-butoxyethyl)pyrrolidone

Into a mixture of 127.7 g (1.5 mol) of 2-pyrrolidone and 0.075 g (0.036 mol % of 2-pyrrolidone) of potassium carbonate, 78.9 g (1.79 mol) of gaseous acetaldehyde were supplied within 3.5 hours, while warming by a water bath at a temperature of 28° C. and stirring vigorously. The reaction mixture was cooled to 5° C. under stirring, and by adding 5 mg of N-($\alpha$-hydroxyethyl)pyrrolidone as the crystallization nuclei to the reaction mixture, the thus formed N-($\alpha$-hydroxyethyl)pyrrolidone was crystallized. On analyzing the thus formed product by liquid chromatography, the conversion ratio of 2-pyrrolidone was 99.0 mol %, and the selectivity in forming N-($\alpha$-hydroxyethyl)pyrrolidone based on 2-pyrrolidone was 100 mol %.

To the thus obtained reaction mixture, a mixed liquid of 1.5 g of sulfuric acid and 400 g of n-butanol was added, thereby dissolving N-($\alpha$-hydroxyethyl)pyrrolidone and reacting the dissolved N-($\alpha$-hydroxyethyl)pyrrolidone.

After finishing the dissolution of N-($\alpha$-hydroxyethyl)pyrrolidone, the temperature of the reaction system was still raised, and the reaction was continued for 30 min while maintaining the temperature at 20° C. On analyzing the reaction product by liquid chromatography, the conversion ratio of 2-pyrrolidone was 95 mol % and the selectivity to N-($\alpha$-hydroxyethyl)pyrrolidone was 5.6 mol %. After neutralizing the reaction mixture by potassium hydroxide, the unreacted N-($\alpha$-hydroxyethyl)pyrrolidone was decomposed into 2-pyrrolidone. On analyzing the reaction product by gas-chromatography, the conversion ratio to 2-pyrrolidone was 89.8 mol %, and the selectivity of N-($\alpha$-n-butoxyethyl)pyrrolidone based on 2-pyrrolidone was 99.9 mol %.

EXAMPLE 2

Synthesis of N-($\alpha$-n-butoxyethyl)pyrrolidone

In the same manner as in Example 1 except for using the starting materials in the respective amounts as shown below, N-($\alpha$-n-butoxyethyl)pyrrolidone was synthesized.

| Starting material | Amount (g) |
| --- | --- |
| 2-pyrrolidone | 85.1 |
| acetaldehyde | 44.9 |
| potassium carbonate | 0.1 |
| n-butanol | 296 and |
| sulfuric acid | 0.5. |

The conversion ratio of 2-pyrrolidone was 96.7 mol %, and the selectivity of N-($\alpha$-hydroxyethyl)pyrrolidone was 3.4 mol %.

After neutralizing the reaction mixture by potassium hydroxide, the reaction mixture was subjected to analysis by gas-chromatography. As the result thereof, the conversion ratio of 2-pyrrolidone was found to be 93.3 mol % and the selectivity of N-($\alpha$-n-butoxyethyl)pyrrolidone based on 2-pyrrolidone was found to be 99.8 mol %.

EXAMPLE 3

Synthesis of N-($\alpha$-n-butoxyethyl)pyrrolidone

To 85.1 g (1 mol) of 2-pyrrolidone, 0.16 g (0.12 mol % to 2-pyrrolidone) of potassium carbonate and 155.8 g (1.8 times by weight of the amount of 2-pyrrolidone) of cyclohexane were added, and the thus formed mixture was vigorously stirred while warming the mixture by a water bath at 28° C. and supplying 44.9 g (1.02 mol) of gaseous acetaldehyde thereinto within 3.5 hours. Then, the reaction mixture was cooled to 8° C. under stirring, and 5 mg of N-($\alpha$-hydroxyethyl)pyrrolidone were added thereto as crystallization nuclei, thereby crystallizing the reaction system.

On analyzing the reaction mixture by liquid chromatography, the conversion ratio of 2-pyrrolidone was 99.6 mol % and the selectivity of N-(α-hydroxyethyl)-pyrrolidone based on 2-pyrrolidone was 100 mol %.

By adding a mixed solution of 0.6 g of sulfuric acid and 296 g of n-butanol, the thus crystallized N-(α-hydroxyethyl)pyrrolidone was reacted while dissolving the crystals thereof.

On analyzing the thus obtained reaction mixture by liquid chromatography, the conversion ratio of 2-pyrrolidone was 99.6 mol % and the selectivity of N-(α-hydroxyethyl)pyrrolidone based on 2-pyrrolidone was 4.0 mol %.

After neutralizing the reaction mixture by potassium hydroxide, the thus neutralized reaction mixture was analyzed by gas-chromatography, and as a result the conversion of 2-pyrrolidone was 95.6 mol % and the selectivity of N-(α-n-butoxyethyl)pyrrolidone was 99.6 mol %.

EXAMPLES 4 to 8

In a similar manner to that in Example 3, N-(α-n-butoxyethyl)pyrrolidone was produced by using the respective amounts of 2-pyrrolidone, acetaldehyde, potassium carbonate, n-butanol and sulfuric acid at the respective reaction temperature in the presence of the respective amounts of the respective kinds of solvents shown in Table 1.

After having neutralized the reaction mixture by potassium hydroxide, the thus neutralized reaction mixture was analyzed by gaschromatography, the results thereof being shown also in Table 1.

TABLE 1

| Example | Amount (g) of 2-pyrrolidone | Amount (g) of acetaldehyde | Ratio of $K_2CO_3$ to 2-pyrrolidone (mol %) | Solvent Kind | Solvent Amount (g) | Reaction temperature (°C.) | Amount (g) of n-butanol | Amount (g) of $H_2SO_4$ | Coversion (mol %) of 2-pyrrolidone | Selectivity (mol %) of N—(α-n-butoxyethyl)-pyrrolidone based on 2-pyrrolidone |
|---|---|---|---|---|---|---|---|---|---|---|
| 4 | 85.1 | 52.5 | 0.036 | Toluene | 85.3 | 25 | 296.0 | 0.6 | 92.4 | 100 |
| 5 | 85.1 | 47.5 | 0.11 | Hexane | 65.9 | 28 | 296.0 | 0.7 | 95.6 | 99.8 |
| 6 | 85.1 | 51.5 | 0.36 | Cyclohexane | 77.9 | 28 | 296.0 | 0.9 | 93.7 | 100 |
| 7 | 170.2 | 92.9 | 0.11 | Cyclohexane | 311.6 | 28 | 593.0 | 1.3 | 95.6 | 100 |
| 8 | 170.2 | 92.3 | 0.15 | Cyclohexane | 311.6 | 28 | 596.0 | 1.3 | 95.9 | 99.7 |

EXAMPLE 9

To 170.2 g (2 mols) of 2-pyrrolidone, 0.41 g (0.15 mol % to 2-pyrrolidone) of potassium carbonate and 331.6 g of cyclohexane were added, and the mixture was vigorously stirred while warming the mixture in a water bath at 28° C. and supplying 94.6 g (2.14 mols) of gaseous acetaldehyde thereinto within 4 hours. The reaction mixture was then cooled to 8° C. under stirring and by adding 5 mg of N-(α-hydroxyethyl)pyrrolidone, as crystallization nuclei, the reaction mixture was subjected to crystallization.

To the thus crystallized reaction mixture, a liquid mixture of 1.3 g of sulfuric acid and 593 g of n-butanol was added, thereby dissolving the crystallized N-(α-hydroxyethyl)pyrrolidone and reacting the thus dissolved N-(α-hydroxyethyl)pyrrolidone. After dissolving N-(α-hydroxyethyl)pyrrolidone, 111.1 g of dried molecular sieve 5A was added to the thus treated reaction mixture, and the reaction was warmed to 20° C. and stirred for 2 hours at the temperature. Thereafter, the reaction mixture was left to stand still for 10 hours.

On analyzing the thus treated reaction mixture by liquidchromatography, the conversion ratio of 2-pyrrolidone was 99.7 mol % and the selectivity of N-(α-hydroxyethyl)pyrrolidone based on 2-pyrrolidone was 2.7 mol %.

After neutralizing the reaction mixture by potassium hydroxide, the thus neutralized reaction mixture was subjected to analysis by gas-chromatography and as a result the conversion ratio of 2-pyrrolidone was 97.0 mol % and the selectivity of N-(α-n-butoxyethyl)pyrrolidone was 100 mol %.

EXAMPLE 10

To 85.1 g (1 mol) of 2-pyrrolidone, 0.15 g (0.11 mol % to 2-pyrrolidone) of potassium carbonate and 155.8 (1.83 times by weight of the amount of 2-pyrrolidone) of cyclohexane were added, and while warming the mixture in a water bath at 28° C. under vigorous agitation, 45.2 g (1.03 mols) of acetaldehyde were supplied into the mixture within 4 hours. The reaction mixture was cooled to 8° C. under stirring and 5 mg of N-(α-hydroxyethyl)pyrrolidone as crystallization nuclei were added to the reaction mixture, thereby crystallizing the reaction mixture.

To the thus crystallized reaction mixture, a liquid mixture of 0.6 g of sulfuric acid and 296 g of n-butanol was addled, thereby dissolving the crystallized N-(α-hydroxyethyl)pyrrolidone and bringing thereof into reaction. Thereafter, cyclohexane and water of the reaction mixture were distilled off by azeotropic distillation from the reaction mixture at 30° C. under a reduced pressure of 100 mmHg. After having carried out the azeotropic dehydration for 2 hours, the pressure on the dehydrated residue was restored to atmospheric pressure, and the temperature of the residue was maintained at 20° C.

On analyzing the residue (the dehydrated reaction mixture) by liquid-chromatography, the conversion ratio of 2-pyrrolidone was 99.1 mol % and the selectivity of N-(α-hydroxyethyl)pyrrolidone based on 2-pyrrolidone was 2.4 mol %.

After having neutralized the reaction mixture by potassium hydroxide, the neutralized reaction mixture was subjected to gaschromatographic analysis and as a result the conversion ratio of 2-pyrrolidone was 97.6 mol % and the selectivity of N-(α-n-butoxyethyl)pyrrolidone based on 2-pyrrolidone was 99.8 mol %.

EXAMPLE 11

Synthesis of N-(α-hydroxyethyl)pyrrolidone

Into a mixture of 85.1 g of 2-pyrrolidone and 0.5 g of sodium carbonate (0.47 mol % per unit molar amount of 2-pyrrolidone), 48.5 g of gaseous acetaldehyde was supplied within 3.5 hours, while being warmed by a water bath of a temperature of 30° C.

After the reaction was over, the reaction mixture was analyzed by liquid chromatography and the reaction ratio of 2-pyrrolidone was 71.5 mol % and the selectivity in forming N-(α-hydroxyethyl)pyrrolidone based on 2-pyrrolidone was 80.5 mol %.

EXAMPLE 12

Synthesis of N-(α-iso-propoxyethyl)pyrrolidone

To 80 g of N-(α-hydroxyethyl)pyrrolidone (0.62 mol), 160.5 g of isopropyl alcohol (2.67 mol) was added and the mixture was stirred at 20° C. to make a solution. 6.1 g of isopropanol solution of 5 wt % sulfuric acid was added to the solution and brought to a reaction for 30 minutes.

After the reaction was over, the reaction mixture was analyzed by a liquid chromatography and the reaction ratio of N-(α-hydroxyethyl)pyrrolidone was 91.4 mol % and the selectivity in forming N-(α-iso-propoxyethyl)pyrrolidone based on N-(α-hydroxyethyl)pyrrolidone was 98.3 mol %.

EXAMPLE 13

Synthesis of N-(α-methoxyethyl)pyrrolidone

To 70 g of N-(α-hydroxyethyl)pyrrolidone (0.54 mol), 70 g of methanol (2.2 mol) was added and the mixture was stirred at 20° C. to make a solution. 2 g of dried Diaion PK 208H (cross-linked polystyrenesulfonic acid resin, made by Mitsubishi Chemical Industries Co.) was added to the solution and after 30 minutes of reaction, the reaction mixture was analyzed with a liquid chromatography. The reaction ratio of N-(α-hydroxyethyl)pyrrolidone was 98.6 mol % and the selectivity in forming N-(α-methoxyethyl)pyrrolidone based on N-(α-hydroxyethyl)pyrrolidone was 99.6 mol %.

EXAMPLE 14

A 200 ml four-necked flask was fitted with a stirrer having a fluorine-resin blade, a gas in-let tube a thermometer and an ice-water-jacketed condenser equipped with a vent, then, a trap containing a small amount of paraffin was connected to the open end of the vent.

To a 100 ml pressure glass vessel equipped with a needle valve, were added 55 g of acetaldehyde, then, the vessel was connected to the gas in-let tube of the flask through a fluorine-resin tube with the needle valve closed.

To the flask, were added 63.8 g of 2-pyrrolidone and 0.4 g of trisodium phosphate decahydrate (0.14 mol % based on the mole of 2-pyrrolidone), and the content was vigorously stirred on a water bath of 30° C. Separately, the vessel containing acetaldehyde was allowed to warm on a water bath of 40° C., and gaseous acetaldehyde was introduced into the reaction system in the flask through the gas in-let tube by opening the needle valve, thereby initiating the reaction.

During the course of the reaction, the needle valve was so controlled that the maximum supplying rate of gaseous acetaldehyde was obtained while taking a caution not to allow gaseous acetaldehyde to escape through the paraffin in the trap.

The time taken to supply 45.2 g of acetaldehyde into the reaction system was 2.5 hours.

After the reaction was over, the reaction mixture was analyzed by liquid chromatography, and the reaction ratio of 2-pyrrolidone was 97.2 mol % and the selectivity in forming N-(α-hydroxyethyl)pyrrolidone based on 2-pyrrolidone was 99.5 mol %.

EXAMPLE 15

A 200 ml four-necked flask was fitted with a stirrer having a fluorine-resin blade, a gas in-let tube a thermometer and an ice-water-jacketed condenser equipped with a vent, then, a trap containing a small amount of paraffin was connected to the open end of the vent.

To a 100 ml pressure glass vessel equipped with a needle valve, were added 55 g of acetaldehyde, then, the vessel was connected to the gas in-let tube of the flask through a fluorine-resin tube with the needle valve closed.

To the flask, were added 63.8 g of 2-pyrrolidone and 0.4 g of sodium orthosilicate (0.29 mol % based on the mole of 2-pyrrolidone), and the content was vigorously stirred on a water bath of 30° C. Separately, the vessel containing acetaldehyde was allowed to warm on a water bath of 40° C., and gaseous acetaldehyde was introduced into the reaction system in the flask through the gas in-let tube by opening the needle valve, thereby initiating the reaction.

During the course of the reaction, the needle valve was so controlled that the maximum supplying rate of gaseous acetaldehyde was obtained while taking a caution not to allow gaseous acetaldehyde to escape through the paraffin in the trap.

The time taken to supply 40.7 g of acetaldehyde into the reaction system was one hour.

After the reaction was over, the reaction mixture was analyzed by liquid chromatography, and the reaction ratio of 2-pyrrolidone was 89.6 mol % and the selectivity in forming N-(α-hydroxyethyl)pyrrolidone based on 2-pyrrolidone was 97.1 mol %.

The reaction mixture was cooled to 0° C. with stirring and 5 mg of N-(α-hydroxyethyl)pyrrolidone was added thereinto as crystallization nuclei. After 10 min., the reaction mixture turned white and solidified. The reaction mixture was analyzed by liquid chromatography, and the reaction ratio of 2-pyrrolidone was 96.5 mol % and the selectivity in forming N-(α-hydroxyethyl)pyrrolidone based on 2-pyrrolidone was 96.3 mol %.

COMPARATIVE EXAMPLE 1

Synthesis of N-(α-hydroxyethyl)pyrrolidone using potassium hydroxide as a catalyst To a 200 ml four-necked flask equipped with a stirrer having a fluorine-resin blade, a thermometer and a reflux condenser, were added 42.6 g of 2-pyrrolidone and 22.1 g of acetaldehyde, then, the mixture was stirred violently.

To the mixture, was added 0.176 g of potassium hydroxide (85% content) and the mixture was heated at 70° C. under reflux for 30 min.

After the reaction was over, the reaction mixture was analyzed by liquid chromatography, and the reaction ratio of 2-pyrrolidone was 28.5 mol % and the selectivity in forming N-(α-hydroxyethyl)pyrrolidone based on 2-pyrrolidone was 43.2 mol %.

COMPARATIVE EXAMPLE 2

Synthesis of N-(α-hydroxyethyl)pyrrolidone using sodium hydroxide as a catalyst

A mixture of 85.1 g of 2-pyrrolidone and 44.1 g of acetaldehyde was stirred vigorously and 0.3 g of sodium hydroxide (0.75 mol % to 2-pyrrolidone) was added to the mixture. The mixture was brought into reaction for 30 minutes at 70° C. under reflux.

After the reaction was over, the reaction mixture was analyzed by a liquid chromatography and the reaction ratio of 2-pyrrolidone was 27.5 mol % and the selectivity in forming N-(α-hydroxyethyl)pyrrolidone based on 2-pyrrolidone was 42.8 mol %.

COMPARATIVE EXAMPLE 3

Synthesis of N-(α-hydroxyethyl)pyrrolidone using polyphosphoric acid as a catalyst A mixture of 85.1 g of 2-pyrrolidone and 1.3 g of polyphosphoric acid was stirred vigorously while being warmed by a water bath of a temperature of 30° C. 44.1 g of gaseous acetaldehyde was charged into the mixture within 3.5 hours.

Immediately after the supply of acetaldehyde was over, the reaction mixture was analyzed by a liquid chromatography. The reaction ratio of 2-pyrrolidone was 87.1 mol % and the selectivity in forming N-(α-hydroxyethyl)pyrrolidone based on 2-pyrrolidone was 43.7 mol %.

What is claimed is:

1. A process for producing a pyrrolidone derivative represented by the general formula (I):

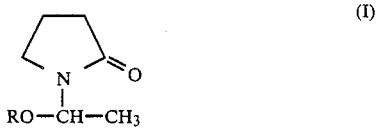

(I)

wherein R is an organic residue obtained by removing hydroxy radical from a $C_{1-10}$ primary alcohol, $C_{1-10}$ secondary alcohol or derivative thereof, comprising:

(1) reacting 2-pyrrolidone with acetaldehyde in the presence of a catalyst which is at least one member selected from the group consisting of potassium carbonate, sodium carbonate, potassium phosphate, sodium phosphate, potassium pyrophosphate, sodium pyrophosphate, potassium silicate and sodium silicate in an amount of 0.0001 to 10 mol % of the catalyst per mole of 2-pyrrolidone, thereby obtaining N-(α-hydroxyethyl)pyrrolidone at a temperature in the range of −10° to 60° C.; and (2) reacting the thus obtained N-(α-hydroxyethyl)-pyrrolidone with a $C_{1-10}$ primary alcohol, a $C_{1-10}$ secondary alcohol or a derivative thereof in the presence of an acidic catalyst selected from the group consisting of an inorganic acid, sulfamic acid, methanesulfonic acid, ethanesulfonic acid, p-toluenesulfonic acid and an acidic ion-exchange resin used in an amount of 0.001 to 10 mol % of the acidic catalyst per mole of N-(α-hydroxyethyl)pyrrolidone at a temperature in the range of −10° to 100° C.

2. The process according to claim 1, wherein R is an organic residue obtained by removing hydroxy radical from methanol, ethanol, n-propanol, n-butanol, n-pentanol, n-hexanol, n-heptanol, n-octanol, isopropyl alcohol, isobutanol, 2-methoxyethanol, 2-ethoxyethanol, 2-propoxyethanol, 2-butoxyethanol, diethylene glycol monomethyl ether, 1,4-butanediol, ethylene glycol, propylene glycol, diethylene glycol and glycerol.

3. The process according to claim 1, wherein R is an organic residue obtained by removing hydroxy from a $C_{1-10}$ aliphatic alcohol.

4. The process according to claim 1, wherein 2-pyrrolidone is in a liquid state and acetaldehyde is in a gaseous state.

5. The process according to claim 4, wherein the gas-liquid contact of said gaseous acetaldehyde and said liquid 2-pyrrolidone is carried out by the continuous supply of said gaseous acetaldehyde into the reaction vessel containing said liquid 2-pyrrolidone.

6. The process according to claim 1, wherein the reaction step (1) is conducted at a temperature ranging from 0° to 50° C.

7. The process according to claim 1, wherein the reaction step (1) is conducted in the presence of toluene, cyclohexane or n-hexane.

8. The process according to claim 7, wherein the amount of solvent employed ranges from 0.01 to 5 times the amount of 2-poyrrolidone reactant.

9. The process according to claim 1, wherein said reaction of N-(α-hydroxyethyl)pyrrolidone and said alcohol or said derivative thereof is carried out at a temperature in the range of 0° to 80° C.

10. The process according to claim 1, wherein water which is formed by the reaction of N-(α-hydroxyethyl)-pyrrolidone and said primary alcohol, secondary alcohol or derivative thereof is removed from the reaction system.

11. The process according to claim 1, wherein said inorganic acid is sulfuric acid, hydrochloric acid, nitric acid or hydrobromic acid.

12. The process according to claim 1, wherein said acidic ion-exchange resin is cross-linked polystyrene sulfonic acid.

13. The process according to claim 1, wherein the amount of said acid catalyst in step (2) of the reaction ranges from 0.001 to 10 moles per unit mole amount of N-(α-hydroxyethyl)pyrrolidone.

14. The process according to claim 1, which further comprises, precipitating N-(α-hydroxyethyl)pyrrolidone product from the reaction medium which forms during step (1), and then further continuing the reaction of step (1).

15. The process according to claim 14, wherein said precipitation of N-(α-hydroxyethyl)pyrrolidone is performed after from 50 to 97 mole % of the 2-pyrrolidone reactant in step (1) has been converted to product.

* * * * *